US011970582B2

United States Patent
Bellan et al.

(10) Patent No.: US 11,970,582 B2
(45) Date of Patent: Apr. 30, 2024

(54) THERMORESPONSIVE FDM PRINTER FILAMENT FOR FORMING VASCULAR CHANNELS IN HYDROGELS

(71) Applicant: Vanderbilt University, Nashville, TN (US)

(72) Inventors: Leon M. Bellan, Nashville, TN (US); John Rector, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 380 days.

(21) Appl. No.: 17/260,979

(22) PCT Filed: Aug. 20, 2019

(86) PCT No.: PCT/US2019/047352
§ 371 (c)(1),
(2) Date: Jan. 15, 2021

(87) PCT Pub. No.: WO2020/041376
PCT Pub. Date: Feb. 27, 2020

(65) Prior Publication Data
US 2021/0292489 A1   Sep. 23, 2021

Related U.S. Application Data

(60) Provisional application No. 62/719,785, filed on Aug. 20, 2018.

(51) Int. Cl.
*B33Y 10/00*   (2015.01)
*B33Y 70/00*   (2020.01)
(Continued)

(52) U.S. Cl.
CPC ............ *C08G 81/024* (2013.01); *B33Y 10/00* (2014.12); *B33Y 70/00* (2014.12); *B33Y 80/00* (2014.12);
(Continued)

(58) Field of Classification Search
None
See application file for complete search history.

(56) References Cited

U.S. PATENT DOCUMENTS

2012/0058174 A1*  3/2012  West .................... A61L 27/38
                                                      424/443
2018/0296343 A1* 10/2018  Wei ..................... B33Y 50/00

FOREIGN PATENT DOCUMENTS

WO       2017175792 A1    10/2017
WO       2018142299 A1     8/2018
WO    WO-2018/142299 A1 *  8/2018

OTHER PUBLICATIONS

Iwan Zein et al.: Fused deposition modeling pf novel scaffold architectures for tissue engineering applications: Biomaterials 23 (2002) pp. 1169-1185 (Year: 2002).*

(Continued)

*Primary Examiner* — Mohammad M Ameen
(74) *Attorney, Agent, or Firm* — Michael Best & Friedrich LLP

(57) ABSTRACT

Provided arm biocompatible polymer compositions, and methods of printing such polymer compositions using a fused deposition modelling printer to form a solid scaffold. In particular, the disclosed compositions may include a thermoresponsive polymer, and the printed scaffold may be used as a sacrificial template providing a three-dimensional vascular structure upon temperature-dependent disintegration. The present compositions and methods may be particularly useful for engineering thick tissues.

8 Claims, 7 Drawing Sheets

(51) Int. Cl.

| | |
|---|---|
| B33Y 80/00 | (2015.01) |
| C08F 218/08 | (2006.01) |
| C08F 226/06 | (2006.01) |
| C08G 65/332 | (2006.01) |
| C08G 81/02 | (2006.01) |
| C08J 3/075 | (2006.01) |
| C12M 1/12 | (2006.01) |
| C12N 5/071 | (2010.01) |

(52) U.S. Cl.
CPC .......... *C08F 218/08* (2013.01); *C08F 226/06* (2013.01); *C08G 65/3322* (2013.01); *C08J 3/075* (2013.01); *C12M 25/14* (2013.01); *C12N 5/069* (2013.01); *C08G 2210/00* (2013.01); *C12N 2513/00* (2013.01); *C12N 2533/30* (2013.01); *C12N 2533/54* (2013.01)

(56) References Cited

OTHER PUBLICATIONS

Iwan Zein et al.: "Fused deposition modeling of novel scaffold architectures for tissue engineering application", Biomaterials 23 (2002) p. 1169-1185 (Year: 2002).*

Hanpin Lim et al.: "Plasticizer effects on physical-mechanical properties of solvent cast Soluplus Films" AAPS PharmSciTech, OL 14, No. 3 Sep. 2013 (Year: 2013).*

Monica Boffito et al. : Thermosensitive block copolymer hydrogels based on poly(e-carpolactone) and polyethylene glycol for biomedical applications: state of the art and future, J Biomed Mater Res Part A 2015: 103A: 1276-1290 (Year: 2015).*

Alhijaj et al. "An investigation into the use of polymer blends to improve the printability of and regulate drug release from pharmaceutical solid dispersions prepared via fused deposition modeling (FDM) 3D printing", European Journal of Pharmaceutics and Biopharmaceutics, vol. 108, 2016, pp. 111-125.

International Search Report and Written Opinion for Application No. PCT/US2019/47352 dated Oct. 29, 2019 (14 pages).

Kolesky et al., "Three-dimensional bioprinting of thick vascularized tissues", PNAS, vol. 113, No. 12, 2016, pp. 3179-3184.

Kolesky et al.,"3D Biopriting of Vascularized, Heterogeneous Cell-Laden Tissue Constructs", Advanced Materials, vol. 26, No. 19, 2014, pp. 3124-3130.

Lee et al., "Development of 3D Microvascular Networks Within Gelatin Hydrogels Using Thermoresponsive Sacrificial Microfibers", Advanced Healthcare Materials, vol. 5, No. 7, 2016, pp. 781-785.

Lim et al., "Plasticizer Effects on Physical-Mechanical Properties of Solvent Cast Soluplus® Films", AAP PharmSciTech, vol. 14, No. 3, 2013, pp. 903-910.

Melocchi et al., "Hot-melt extruded filaments based on pharmaceutical grade polymers for 3D printing by fused deposition modeling", International Journal of Pharmaceutics, vol. 509, 2016, pp. 255-263.

Zein et al., "Fused deposition modeling of novel scaffold architectures for tissue engineering applications", Biomaterials, vol. 23, 2002, pp. 1169-1185.

Zhang et al., "Coupling 3D printing with hot-melt extrusion to produce controlled-release tablets", International Journal of Pharmaceutics, vol. 519, No. 1-2, 2017, pp. 186-197.

* cited by examiner

THERMORESPONSIVE FDM PRINTER FILAMENT FOR FORMING VASCULAR CHANNELS IN HYDROGELS

CROSS-REFERENCE TO RELATED APPLICATIONS

This patent application is the U.S. national stage entry, under 35 U.S.C. § 371, of International Application Number PCT/US2019/047352, filed Aug. 20, 2019, which claims the benefit of and priority to U.S. Provisional Application No. 62/719,785, filed Aug. 20, 2018, the entire contents of each of which are hereby incorporated by reference.

STATEMENT OF GOVERNMENT INTEREST

This invention was made with government support under Grant number 1506717 awarded by the National Science Foundation (NSF). The government has certain rights in the invention.

INTRODUCTION

Additive manufacturing approaches have significant potential to revolutionize the field of tissue engineering, and are increasingly being used to pattern both cells and void spaces in engineered tissue constructs. In order to maintain cell viability in thick engineered tissue, a vascular network of fluidic channels is required. When perfused, an artificial vasculature can provide necessary soluble compound exchange to all embedded cells. While additive manufacturing approaches have been used to produce sacrificial templates to form such channels, they currently require expensive and complex hardware (which hinders widespread use), and rely upon fugitive gel inks with limited mechanical properties (which hinders the production of fine or complex geometries).

One of the most significant hurdles currently holding back the progress of tissue engineering is the production of a 3D vasculature throughout thick artificial tissue constructs. Thin engineered tissue constructs have limited utility for clinical or research needs due to their inability to appropriately mimic the quantity, density, and organizational complexity of desired cells. Any engineered tissue construct of significant thickness (greater than a few hundred microns) that contains metabolizing, functional cells must also include an artificial vasculature that allows, via perfusion, delivery of necessary soluble compounds to all cells throughout the scaffold volume. Without such a vasculature, cells will die from ischemia, leading to a necrotic core within the engineered tissue that limits the utility of the construct for regenerative or research applications. It is still, however, a major engineering challenge for most researchers to form channel networks in hydrogels, and because there is no one widespread approach to this fabrication need, there is still room to develop a simple, inexpensive, and robust system to form these structures.

SUMMARY

In one aspect, the present disclosure provides a method for preparing a solid scaffold, the method comprising: printing a biocompatible polymer composition comprising a thermoresponsive polymer using a fused deposition modelling printer to form the solid scaffold.

The solid scaffold disclosed herein may comprise vascular branches, which define a 3-dimensional vascular structure. The solid scaffold may be used a sacrificial template for tissue engineering. In some embodiments, provided herein are methods of manufacturing a tissue comprising: contacting the solid scaffold as disclosed herein with a plurality of cells within a matrix; and culturing the cells.

In another aspect, the present disclosure provides a biocompatible polymer composition comprising a thermoresponsive polymer and a plasticizer, wherein the composition is capable of being printed by fused deposition modelling.

In another aspect, the present disclosure provides a three-dimensional vascular structure comprising a biocompatible polymer composition comprising a thermoresponsive polymer.

BRIEF DESCRIPTION OF THE DRAWINGS

FIGS. 3A and 3D show CAD design of two varieties of branching channel structures. FIGS. 3B and 3E show the 3D printed sacrificial thermoresponsive templates made from plasticized Soluplus®. FIGS. 3C and 3F show the channels formed in gelatin hydrogel perfused with a concentrated solution of green fluorescent beads (scale bars are 2 mm).

DETAILED DESCRIPTION

Figure 1A:
FIG. 1A shows an extruded plasticized Soluplus® filament (1.75 mm diameter) to be used in a typical FDM printer.

Disclosed herein are polymer materials (such as polymer filaments) which may be used in an FDM-style 3D printer (e.g., Makerbot, RepRap, Stratasys, etc.) and may serve as a sacrificial template in cell-laden matrix (such as hydrogels). The materials described herein may be printed with high resolution, and may dissolve in cold aqueous solutions but not warm aqueous solutions, enabling a temperature-triggered process to form channels in hydrogels. Because the components of the materials are biocompatible, the materials do not cause any harm to cells within the engineered tissue construct. In particular, the present disclosure relates to FDM printing of a thermoresponsive material to form a sacrificial template or scaffold. For example, the materials disclosed herein may be used to make vasculature in an engineered tissue construct using a simple FDM 3D printer known in the art.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "biocompatible" refers to a composition that is not toxic to a living cell, such as a human cell. For example, the composition may be compatible with, and cause no harmful effect to, the normal life cycle of the cell, including cellular growth and division, signal transduction, and physiological functions.

The term "disintegration temperature" refers to a temperature or a temperature range, below which a polymer composition changes its physical form from a solid, semi-solid, or gel state to a liquid state. As an example, the polymer composition may be hydrated (such as by being embedded in an aqueous or moisturized environment, e.g., a hydrogel matrix), and may maintain a solid or gel state above the disintegration temperature. As the temperature reduces below the disintegration temperature, the polymer composition may become a liquid and/or dissolved in the water from the environment, thus becoming "disintegrated" as compared to its original state above the disintegration temperature. The disintegrated polymer composition may be removed from the environment (e.g., a hydrogel matrix) by rinsing or perfusion of the environment.

The term "fused deposition modelling" generally refers to a printing process in which objects are formed by layering fusible material in a controlled manner such that a desired three dimensional shape can be created. This process also may be referred to as "additive printing." Typically in a fused deposition modeling process a fused deposition modeling printer is used. For example, the printer may have a three dimensionally moveable print head. The fusible material may be fed into the print head in the form of filaments. In a typical process, the print head heats up the fusible filament which is subsequently melted, extruded from the print head and deposited as multiple layers (e.g., one layer sequentially deposited on top of another previously deposited layer). The printed object then may be allowed to cool down and solidify. Thus a fused deposition modeled object may grow with each deposited layer and gradually attains its desired shape.

The term "thermoresponsive polymer" refers to a polymer having a physical or chemical property that undergoes a discontinuous or binary change in a temperature-dependent manner. For example, the physical conformation or polarity of a thermoresponsive polymer may change in a temperature-dependent manner, and the thermoresponsive polymer exhibits a first conformation below a threshold temperature and a second, substantially different conformation above the threshold temperature. In a particular example, a thermoresponsive polymer exhibits an expanded coil or chain confirmation below a lower critical solution temperature (LCST) temperature, and exhibits a compact or globular conformation above such threshold temperature. The thermoresponsive behavior also may be observed when such polymer is placed in an aqueous environment. For example, the polymer may be in contact with, or is embedded in a hydrated matrix (such as an aqueous solution or a hydrogel) and may exhibit a thermoresponsive behavior such that they are hydrophobic and insoluble above the LCST, and become hydrophilic and soluble below the LCST. When warmed, the thermoresponsive polymer may undergo a reversible hydrated-coil to hydrophobic-globule transition as the temperature increases beyond the LCST, and above a critical concentration this results in a macroscopic, reversible sol-→gel transition.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated

2. METHOD

Thermoresponsive polymers may be biocompatible and combined with the cooling-triggered disintegration behavior they exhibit can facilitate the production of well-defined vasculature without exposing cells to harsh environments. Fused deposition modeling (FDM) printing is an established technique to form 3D structures using molten polymer, and is capable of producing fine, complex features. Currently, no FDM-based printing process has been established to pattern thermoresponsive polymers. In particular, most thermoresponsive polymers do not inherently exhibit properties (e.g. melt temperature, melt flow viscosity, plasticity) appropriate for FDM processes.

While current aqueous-soluble filament material such as polyvinyl alcohol (PVA) and high impact polystyrene (HIPS) may facilitate the production of complex solid polymer geometries, a thermoresponsive (with appropriate transition temperature, $T_{tr}$), non-toxic sacrificial material is needed to produce void spaces in cell-laden hydrogels without compromising cell viability. To date, no FDM filament with these properties has been identified. Thus, there is a significant need for FDM printing processes and materials, such as suitable thermoresponsive polymer filaments, for producing sacrificial structures, not only to aid in fabricating solid structural parts but also to assist in providing a template for living biomaterials for tissue engineering.

In one aspect, provided is a method of method for preparing a solid scaffold, the method comprising:
  printing a biocompatible polymer composition comprising a thermoresponsive polymer using a fused deposition modelling printer to form the solid scaffold.

In some embodiments, the biocompatible polymer composition has a disintegration temperature, wherein the polymer composition is in a solid or gel state above the disintegration temperature, and wherein the polymer composition is in a liquid state below the disintegration temperature. The disintegration temperature may be at least 0° C., at least 5° C., at least 10° C., at least 15° C., at least 20° C., at least 25° C., at least 30° C., or at least 35° C. The disintegration temperature may be less than 40° C., less than 35° C., less than 30° C., less than 25° C., less than 20° C., less than 15° C., less than 10° C., or less than 5° C. In some embodiments, the disintegration temperature is about 0° C. to about 40° C., such as about 4° C. to about 37° C., about 4° C. to about 36° C., about 4° C. to about 35° C., about 4° C. to about 34° C., about 4° C. to about 33° C., about 4° C. to about 32° C., about 4° C. to about 31° C., about 4° C. to about 30° C., about 5° C. to about 30° C., about 5° C. to about 25° C., or about 5° C. to about 20° C. In some embodiments, the disintegration temperature is about 4° C. to about 37° C. In some embodiments, the disintegration temperature is about 5° C., about 10° C., about 15° C., about 20° C., about 25° C., about 30° C., or about 35° C.

The thermoresponsive polymer may include any thermoresponsive polymer which may be suitably used as a feed material for a FDM printing process described herein and is biocompatible for culturing living cells. In some embodiments, the thermoresponsive polymer comprises a monomer selected from the group consisting of N-isopropylacrylamide, N,N-diethylacrylamide, 2-(dimethylamino)ethyl methacrylate, glucose, O-methyl glucose, lactic acid, glycolic acid, caprolactone, vinyl caprolactam, vinyl acetate, ethylene glycol, and a combination thereof.

In some embodiments, the thermoresponsive polymer comprises a monomer selected from the group consisting of N-isopropylacrylamide, N,N-diethylacrylamide, 2-(dimethylamino)ethyl methacrylate, and a combination thereof. For example, the thermoresponsive polymer may be poly(N-isopropylacrylamide), poly(N,N-diethylacrylamide), poly[2-(dimethylamino)ethyl methacrylate], or a copolymer of N-isopropylacrylamide with one or more monomer selected from the group consisting of acrylamide, N-tert-butylacrylamide, acrylic acid, and allylamine.

In some embodiments, the thermoresponsive polymer comprises a monomer selected from the group consisting of vinyl caprolactam, vinyl acetate, ethylene glycol, and a combination thereof. In some embodiments, the thermoresponsive polymer is a poly(N-vinylcaprolacatam). In some embodiments, the thermoresponsive polymer is a copolymer comprising vinyl caprolactam, vinyl acetate, ethylene glycol, or a combination thereof. In some embodiments, the thermoresponsive polymer is a copolymer comprising vinyl caprolactam and vinyl acetate, or a copolymer comprising vinyl caprolactam and ethylene glycol. In some embodiments, the thermoresponsive polymer is a copolymer comprising vinyl caprolactam, vinyl acetate, and ethylene glycol. In some embodiments, the thermoresponsive polymer is a graft copolymer comprising vinyl caprolactam, vinyl acetate, ethylene glycol, or a combination thereof. In some embodiments, the thermoresponsive polymer is a graft copolymer comprising vinyl caprolactam and vinyl acetate, or a graft copolymer comprising vinyl caprolactam and ethylene glycol. In particular embodiments, the thermoresponsive polymer is a graft copolymer comprising vinyl caprolactam, vinyl acetate, and ethylene glycol. For example, the thermoresponsive polymer may be a polyvinyl caprolactam-polyvinyl acetate-polyethylene glycol graft copolymer, such as the commercial product Soluplus® (BASF, Ludwigshafen, Germany).

In some embodiments, the thermoresponsive polymer comprises a monomer selected from the group consisting of glucose, O-methyl glucose, lactic acid, glycolic acid, caprolactone, and a combination thereof. For example, the thermoresponsive polymer may be cellulose, methylcellulose, poly(N-vinylcaprolacatam), polylactic acid, polyglycolic acid, poly(lactic-co-glycolic acid), or polycaprolactone.

In some embodiments, the thermoresponsive polymer comprises poly(N-isopropylacrylamide), poly(N,N-diethylacrylamide), poly[2-(dimethylamino)ethyl methacrylate], cellulose, methylcellulose, poly(N-vinylcaprolacatam), polylactic acid, polyglycolic acid, poly(lactic-co-glycolic acid), polycaprolactone, a copolymer of N-isopropylacrylamide with one or more monomer selected from the group consisting of acrylamide, N-tert-butylacrylamide, acrylic acid, and allylamine, a copolymer comprising at least one monomer selected from group consisting of vinyl caprolactam, vinyl acetate, and ethylene glycol, or a combination thereof.

In some embodiments, the thermoresponsive polymer comprises a copolymer comprising at least one monomer selected from the group consisting of vinyl caprolactam, vinyl acetate, and ethylene glycol.

In some embodiments, the thermoresponsive polymer comprises a polyvinyl caprolactam-polyvinyl acetate-polyethylene glycol graft copolymer.

Suitable thermoresponsive polymers may have a glass transition temperature ($T_g$) of about 50° C. to about 100° C., such as about 50° C., about 60° C., about 70° C., about 80° C., about 90° C., or about 100° C. The glass transition temperature ($T_g$) may be less than 100° C., less than 90° C., less than 80° C., less than 70° C., or less than 60° C. The glass transition temperature ($T_g$) may be greater than 50° C., greater than 60° C., greater than 70° C., greater than 80° C., or greater than 90° C.

As non-limiting examples, suitable thermoresponsive polymers may include those that do not degrade at a temperature of at least 100° C. In some embodiments, the thermoresponsive polymer is stable and does not degrade at a temperature above 100° C., above 150° C., above 200° C., above 250° C., above 270° C., or above 300° C. In particular embodiments, the thermoresponsive polymer comprises Soluplus®, which is amorphous with a glass transition temperature of about 68° C. to 70° C. and degrades at approximately 278° C.

In some embodiments, the biocompatible polymer composition further comprises a plasticizer. The plasticizers may be any non-volatile compounds which improve the flexibility and processability of the polymer composition disclosed herein, for example, by decreasing the glass transition temperature. Suitable plasticizers for the polymer compositions disclosed herein include those that do not demonstrate toxicity to living cells. Addition of a plasticizer may lead to multiple effects, including a reduction in viscosity, increased elongation, decreased tensile strength, and improving the impact resistance and resistance to fracture.

In some embodiments, the plasticizer comprises polyethylene glycol, acetyltributyl citrate, propylene glycol, glycerol, polyoxyl castor oil, a poloxamer, or a combination thereof. Other examples of plasticizers include plasticizing zein, hydroxypropyl cellulose, poly(lactic acid) (PLA) and poly(3-hydroxybutyrate) (PHB) blends, and PLA and acrylonitrile butadiene styrene (ABS) composites. In some embodiments, the plasticizer comprises one or more polyethylene glycols, such as PEG300, PEG1000, PEG5000, or PEG100000. In some embodiments, the plasticizer comprises polyoxyl castor oil, such as Kolliphor® RH 40 (BASF, CAS No. 61788-85-0). In some embodiments, the plasticizer comprises a poloxamer, such as Kolliphor® P188 (BASF, CAS No. 9003-11-6). In some embodiments, the plasticizer comprises glycerol.

The thermoresponsive polymer and the plasticizer may be a mixture at any ratio to achieve a desired property, for example, the disintegration temperature of the biocompatible polymer composition and/or FDM printing results. In some embodiments, the thermoresponsive polymer and the plasticizer may be present at ratio of 1:99 to 99:1 by weight. This includes, for example a thermoresponsive polymer to plasticizer ratio of about 10:90; about 30:70, about 50:50, about 70:30, about 90:10, about 95:5, or about 99:1. The thermoresponsive polymer to plasticizer ratio may be at least 10:90, at least 30:70, at least 50:50, at least 70:30, at least 90:10, or at least 95:5. The thermoresponsive polymer to plasticizer ratio may be less than 99:1, less than 95:5, less than 90:10, less than 70:30, less than 50:50, or less than 30:70. Adjusting the thermoresponsive polymer to plasticizer ratio to achieve an appropriate value may be accomplished using techniques known in the art. In some embodiments, the thermoresponsive polymer is Soluplus®, and the thermoresponsive polymer to plasticizer ratio is about 90:10, about 95:5, or about 99:1. In particular embodiments, the thermoresponsive polymer is Soluplus®, the plasticizer includes one or more polyethylene glycols, and the thermoresponsive polymer to plasticizer ratio is about 90:10. For example, the polymer composition may include Soluplus® at about 90% by weight, PEG300 (Mw 300) at about 7% by weight, and PEG100000 (Mw 100,000) at about 3% by weight.

In some embodiments, the biocompatible polymer composition is in a form of filament, e.g., a filament suitable for printing using an FDM printer. The filament may have a diameter of about 50 μm to about 2000 μm, such as about 100 μm to about 2000 μm, about 500 μm to about 2000 μm, or about 500 μm to about 1500 μm. In some embodiments, the filament has a diameter of 200 μm or lower, such as about 50 μm, about 100 μm, or about 150 μm. In some embodiments, the filament has a diameter greater than 200 μm, such as about 500 μm, about 1000 μm, or about 1500 μm. In some embodiments, the filament has a diameter of about 500 μm to about 1500 μm.

In some embodiments, the biocompatible polymer composition is a filament having a melt viscosity suitable for a 3D FDM printing process as disclosed herein. In some embodiments, the filament has a melt viscosity of about 50 Pa·s to about 200,000 Pa·s, including but not limited to about 100 Pa·s to about 200,000 Pa·s, about 1,000 Pa·s to about 200,000 Pa·s, about 5,000 Pa·s to about 200,000 Pa·s, about 10,000 Pa·s to about 200,000 Pa·s, or about 50,000 Pa·s to about 200,000 Pa·s. The melt viscosity may be less than 200,000 Pa·s, less than 150,000 Pa·s, less than 100,000 Pa·s, or less than 50,000 Pa·s. The melt viscosity may be more than 50 Pa·s, more than 100 Pa·s, more than 1,000 Pa·s, more than 5,000 Pa·s, more than 10,000 Pa·s, more than 50,000 Pa·s, more than 100,000 Pa·s, or more than 150,000 Pa·s.

The printing process as disclosed herein may be carried out at a temperature of about 50° C. to about 250° C. In some embodiments, the printing is performed at a temperature of about 60° C. to about 200° C., about 80° C. to about 200° C., about 100° C. to about 200° C., or about 120° C. to about 200° C. In some embodiments, the printing is performed at a temperature of about 100° C. to about 200° C. The temperature may be greater than 100° C., greater than 120° C., greater than 130° C., greater than 140° C., greater than 150° C., greater than 160° C., greater than 170° C., greater than 180° C., greater than 190° C., or greater than 200° C. The temperature may be less than 200° C., less than 190° C., less than 180° C., less than 170° C., less than 160° C., less than 150° C., less than 140° C., less than 130° C., or less than 120° C.

In some embodiments, the printed solid scaffold disclosed herein comprises vascular branches, which define a 3-dimensional vascular structure. In some embodiments, the vascular branches have a diameter of about 50 μm to about 5000 μm, including but not limited to about 100 μm, about 200 μm, about 300 μm, about 500 μm, about 1000 μm, about 1500 μm, about 2000 μm, about 2500 μm, about 3000 μm, or about 4000 μm. The diameter may be greater than 100 μm, greater than 200 μm, greater than 300 μm, greater than 500 μm, greater than 1000 μm, greater than 1500 μm, greater than 2000 μm, greater than 2500 μm, or greater than 3000 μm. The diameter may be less than 4000 μm, less than 3000 μm, less than 2500 μm, less than 2000 μm, less than 1500 μm, less than 1000 μm, less than 500 μm, less than 200 μm, or less than 100 μm.

In another aspect, provided is a solid scaffold produced by the method disclosed herein. The solid scaffold may be printed using a biocompatible polymer composition comprising a thermoresponsive polymer as disclosed herein. In particular embodiments, the solid scaffold may be printed from a polymer composition comprising a polyvinyl caprolactam-polyvinyl acetate-polyethylene glycol graft copolymer (such as Soluplus®) using an FDM printer. The polymer composition may further comprise a suitable plasticizer.

In another aspect, provided is a method of manufacturing a tissue comprising:

contacting a solid scaffold as described herein with a plurality of cells within a matrix; and
culturing the cells.

In some embodiments, the printed solid scaffold disclosed herein may be embedded in a matrix, which is laden with cells to be cultured. In particular embodiments, the matrix is a hydrogel, such as a crosslinked gelatin gel. The cell-laden matrix may be prepared using techniques known in the art. In some embodiments, the cell-laden matrix (such as a gel) is cast over the solid scaffold, and the mixture is incubated to allow crosslinking of the matrix material (such as crosslinking of gelatin catalyzed by transglutaminase).

The solid scaffold disclosed herein may serve as a sacrificial template, which upon disintegration provide a three-dimensional network of vascular channels defined by the vascular structure (e.g., branches with micrometer scale diameters) of the solid scaffold. For example, the composite material formed by the cell-laden matrix and the solid scaffold may be exposed to a reduced temperature below the disintegration temperature of the biocompatible polymer composition, from which the solid scaffold is formed by FDM printing. The reduced temperature may cause the polymer composition to transform to a liquid state and/or dissolve in the surrounding aqueous solution. Subsequently, the disintegrated scaffold may be removed from the matrix by rinsing or perfusion, thereby leaving behind a network of vascular channels which may serve as vasculature structure for tissue culture.

Advantageously, using the method disclosed herein, cells may be mixed in the hydrogel prior to casting or introduced via flow into the microchannels after they are fabricated. The microchannel architecture (as defined by the 3D structure of the sacrificial scaffold or template) is dictated not by self-assembly of the cells, but by the researcher or by the fabrication process. These microfluidic matrix (e.g., hydrogel) approaches may provide immediate convective transport of soluble compounds through the microfluidic channel network, and may thus support all embedded cells instantly.

Remarkably, the method disclosed herein provide a convenient and effective alternative to the existing "bottom-up" approaches, which use the natural ability of endothelial cells to form lumen networks via angiogenic sprouting and/or vasculogenesis but are generally slow and difficult for the engineering of thick tissues. In contrast, by constructing a thick scaffold, the method disclosed herein may provide a deeper perfusable volume to deliver necessary soluble compounds (nutrients and oxygen) to cells embedded deep within the engineered tissue, than avoiding formation of a necrotic core. Thus, the method disclosed herein may offer superior results over the conventional approaches in thick engineered tissue by reducing diffusion limitations in the thickness direction, and may have improved clinical utility by incorporating significant heterogeneity or complexity in the thickness direction.

While additive manufacturing approaches have been used to produce sacrificial templates that form such channel networks, these approaches currently require complex, expensive hardware (hindering widespread use), and rely upon fugitive gel inks with limited mechanical properties (hindering the production of fine or complex geometries). In comparison, the method disclosed herein uses FDM printing in a robust process that produces solid structures with complex geometries (e.g., using polymer filaments fed through a heated extruder). Remarkably, the method disclosed herein may produce thermoresponsive sacrificial structures (which dissolve only below a critical temperature threshold) with high resolution using FDM printing technology.

3. POLYMER COMPOSITION

In another aspect, provided is a biocompatible polymer composition comprising a thermoresponsive polymer and a plasticizer, wherein the composition is capable of being printed by fused deposition modelling.

The thermoresponsive polymer may comprises a monomer selected from the group consisting of N-isopropylacrylamide, N,N-diethylacrylamide, 2-(dimethylamino)ethyl methacrylate, glucose, O-methyl glucose, lactic acid, glycolic acid, caprolactone, vinyl caprolactam, vinyl acetate, ethylene glycol, and a combination thereof.

In some embodiments, the thermoresponsive polymer comprises a monomer selected from the group consisting of N-isopropylacrylamide, N,N-diethylacrylamide, 2-(dimethylamino)ethyl methacrylate, and a combination thereof. For example, the thermoresponsive polymer may be poly(N-isopropylacrylamide), poly(N,N-diethylacrylamide), poly[2-(dimethylamino)ethyl methacrylate], or a copolymer of N-isopropylacrylamide with one or more monomer selected from the group consisting of acrylamide, N-tert-butylacrylamide, acrylic acid, and allylamine.

In some embodiments, the thermoresponsive polymer comprises a monomer selected from the group consisting of vinyl caprolactam, vinyl acetate, ethylene glycol, and a combination thereof. In some embodiments, the thermoresponsive polymer is a poly(N-vinylcaprolacatam). In some embodiments, the thermoresponsive polymer is a copolymer comprising vinyl caprolactam, vinyl acetate, ethylene glycol, or a combination thereof. In some embodiments, the thermoresponsive polymer is a copolymer comprising vinyl caprolactam and vinyl acetate, or a copolymer comprising vinyl caprolactam and ethylene glycol. In some embodiments, the thermoresponsive polymer is a copolymer comprising vinyl caprolactam, vinyl acetate, and ethylene glycol. In some embodiments, the thermoresponsive polymer is a graft copolymer comprising vinyl caprolactam, vinyl acetate, ethylene glycol, or a combination thereof. In some embodiments, the thermoresponsive polymer is a graft copolymer comprising vinyl caprolactam and vinyl acetate, or a graft copolymer comprising vinyl caprolactam and ethylene glycol. In particular embodiments, the thermoresponsive polymer is a graft copolymer comprising vinyl caprolactam, vinyl acetate, and ethylene glycol. For example, the thermoresponsive polymer may be a polyvinyl caprolactam-polyvinyl acetate-polyethylene glycol graft copolymer, such as the commercial product Soluplus®.

In some embodiments, the thermoresponsive polymer comprises a monomer selected from the group consisting of glucose, O-methyl glucose, lactic acid, glycolic acid, caprolactone, and a combination thereof. For example, the thermoresponsive polymer may be cellulose, methylcellulose, poly(N-vinylcaprolacatam), polylactic acid, polyglycolic acid, poly(lactic-co-glycolic acid), or polycaprolactone.

In some embodiments, the thermoresponsive polymer comprises poly(N-isopropylacrylamide), poly(N,N-diethylacrylamide), poly[2-(dimethylamino)ethyl methacrylate], cellulose, methylcellulose, poly(N-vinylcaprolacatam), polylactic acid, polyglycolic acid, poly(lactic-co-glycolic acid), polycaprolactone, a copolymer of N-isopropylacrylamide with one or more monomer selected from the group consisting of acrylamide, N-tert-butylacrylamide, acrylic acid, and allylamine, a copolymer comprising at least one monomer selected from group consisting of vinyl caprolactam, vinyl acetate, and ethylene glycol, or a combination thereof.

In some embodiments, the thermoresponsive polymer comprises a copolymer comprising at least one monomer selected from the group consisting of vinyl caprolactam, vinyl acetate, and ethylene glycol.

In some embodiments, the thermoresponsive polymer comprises a polyvinyl caprolactam-polyvinyl acetate-polyethylene glycol graft copolymer.

In some embodiments, either hydrophobic or hydrophilic plasticizers with varying molecular weight may be used in the method disclosed herein to influence the plasticizer-polymer and plasticizer-solvent interactions, as well as the temperature-responsive macroscopic disintegration and eventual dissolution of printed structures in solution. The plasticizers may affect the mechanical properties and swelling of the printed scaffold, and may influence feature fidelity throughout the sacrificial template-based fabrication process. In some embodiments, the plasticizer comprises polyethylene glycol, acetyltributyl citrate, propylene glycol, glycerol, polyoxyl castor oil, a poloxamer, or a combination thereof. In some embodiments, the plasticizer comprises one or more polyethylene glycols, such as PEG300, PEG1000, PEG5000, or PEG100000. In some embodiments, the plasticizer comprises polyoxyl castor oil, such as Kolliphor® RH 40 (BASF, CAS No. 61788-85-0). In some embodiments, the plasticizer comprises a poloxamer, such as Kolliphor® P188 (BASF, CAS No. 9003-11-6). In some embodiments, the plasticizer comprises glycerol.

In some embodiments, the thermoresponsive polymer and the plasticizer may be present at ratio of 1:99 to 99:1 by weight. This includes, for example a thermoresponsive polymer to plasticizer ratio of about 10:90; about 30:70, about 50:50, about 70:30, about 90:10, about 95:5, or about 99:1. The thermoresponsive polymer to plasticizer ratio may be at least 10:90, at least 30:70, at least 50:50, at least 70:30, at least 90:10, or at least 95:5. The thermoresponsive polymer to plasticizer ratio may be less than 99:1, less than 95:5, less than 90:10, less than 70:30, less than 50:50, or less than 30:70. In some embodiments, the thermoresponsive polymer is Soluplus®, and the thermoresponsive polymer to plasticizer ratio is about 90:10, about 95:5, or about 99:1. In particular embodiments, the thermoresponsive polymer is Soluplus®, the plasticizer includes one or more polyethylene glycols, and the thermoresponsive polymer to plasticizer ratio is about 90:10. For example, the polymer composition may include Soluplus® at about 90% by weight, PEG300 (Mw 300) at about 7% by weight, and PEG100000 (Mw 100,000) at about 3% by weight.

In some embodiments, the biocompatible polymer composition is in a form of filament, e.g., a filament suitable for printing using an FDM printer. The filament may have a diameter of about 50 µm to about 2000 µm, such as about 100 µm to about 2000 µm, about 500 µm to about 2000 µm, or about 500 µm to about 1500 µm. In some embodiments, the filament has a diameter of 200 µm or lower, such as about 50 µm, about 100 µm, or about 150 µm. In some embodiments, the filament has a diameter greater than 200 µm, such as about 500 µm, about 1000 µm, or about 1500 µm. In some embodiments, the filament has a diameter of about 500 µm to about 1500 µm.

In some embodiments, the polymer compositions (e.g. filaments) as described herein may be printed into sacrificial templates with high resolution to make vasculature in an engineered tissue construct using a simple 3D FDM printer (<$1k) known in the art.

In particular embodiments, biocompatible polymer filament materials may be used in any FDM-style 3D printer (Makerbot, RepRap, Stratasys, etc.) and may be printed into a sacrificial template in cell-laden hydrogels. The filament described herein may be printed with high resolution, and may dissolve in cold aqueous solutions but not warm aqueous solutions, enabling a temperature-triggered process to form channels in hydrogels. Because the components of the filament are biocompatible, the material does not cause any harm to cells within the engineered tissue construct.

In some embodiments, the mechanical properties of the filament material as disclosed herein may be offer superior results to the known materials for printing vascular channels (e.g. Pluronic F127, which is in a gel form at room temperature but dissolves at 4° C.). As a result, the polymer compositions (e.g., filament) disclosed herein may provide better structures with finer resolution and more complexity.

In another aspect, provided is a three-dimensional vascular structure comprising a biocompatible polymer composition comprising a thermoresponsive polymer. The biocompatible polymer compositions and the thermoresponsive polymers may include those suitable for being printed by fused deposition modelling as described herein. In some embodiments, the three-dimensional vascular structure comprises vascular branches having a diameter of about 50 µm to about 5000 µm, including but not limited to about 100 µm, about 200 µm, about 300 µm, about 500 µm, about 1000 µm, about 1500 µm, about 2000 µm, about 2500 µm, about 3000 µm, or about 4000 µm. The diameter may be greater than 100 µm, greater than 200 µm, greater than 300 µm, greater than 500 µm, greater than 1000 µm, greater than 1500 µm, greater than 2000 µm, greater than 2500 µm, or greater than 3000 µm. The diameter may be less than 4000 µm, less than 3000 µm, less than 2500 µm, less than 2000 µm, less than 1500 µm, less than 1000 µm, less than 500 µm, less than 200 µm, or less than 100 µm. In some embodiments, the three-dimensional vascular structure have a disintegrating temperature (e.g., about 4° C. to about 37° C.), and may form a 3-dimensional network of vascular channels when being exposed to a reduced temperature.

4. EXAMPLES

Materials and Methods

Soluplus®, a polyvinyl caprolactam-polyvinyl acetate-polyethylene glycol graft copolymer is a product of BASF. Other chemicals were obtained from Sigma Aldrich or Fisher Scientific. Fused deposition modelling (FDM) printing was performed on a FlashForge Creator Pro printer.

Example 1 Preparation of SoluBlend Filament and Sacrificial Scaffold

A thermoresponsive, non-toxic 3D printable filament was produced, which was compatible with a gear-fed, heated extrusion nozzle for fused deposition modeling (tested on the FlashForge Creator Pro). The filament was made in 40 g batches with a mass ratio of 94% Soluplus® to 6% plasticizer, chosen from PEG 300, acetyl tributyl citrate (ATBC), or glycerol. In a chemical fume hood, dry Soluplus® was slowly added to 80 ml of dichloromethane (DCM) and mixed with a magnetic stir bar. More DCM were added if the solution became very viscous from evaporation. Once the Soluplus® is completely dissolved, the plasticizer was then added into the solution and stirred for 10 minutes. When glycerol was used as plasticizer, methanol rather than DCM was use as solvent. The mixture was then poured into four, custom polydimethylsiloxane (PDMS) dishes, measuring about 75 mm in diameter. The dishes were placed in the fume hood to evaporate overnight. The mixtures solidified into solid disks at this point and were removed from the PDMS dishes. To evaporate the remaining solvent, the disks were placed in a vacuum oven at 60° C. and full vacuum for a minimum of 4 hours. The dried disks are broken into large pieces by hand and then quickly pulverized using an IKA® A11 Basic blender, resulting in polymer pieces ranging in size from a small gravel to a fine powder.

The polymer was fed into a Filabot EX2 filament extruder. The Filabot was run at a temperature of 130° C. with the feed rate continuously adjusted to produce a filament with diameter ranging from 1.60-1.90 mm. The polymer material was added in small batches at a time in order to prevent gumming up the machine. Half of the material was fed into the Filabot and extruded in order to clear out any old material (which was not used for printing). The second half of the material was extruded and collected on a spool. The filament was then measured and any portion with diameter outside the 1.60-1.90 mm range was cut and removed. The filament which passed inspection was stored in a desiccator until ready to be printed.

The filament was briefly rehydrated to prevent cracking and breaking before being fed into a 3D printer. This was done by putting the filament in an open petri dish and placing this into a humid cell culture incubator, such as the Heracell 150i, for 10 minutes. The filament was then removed and fed into a benchtop FDM 3D printer and printed at a head temperature of 160-180° C. Typically, the filament was printed into a predetermined shape with a 3D vascular structure.

Figure 1B:
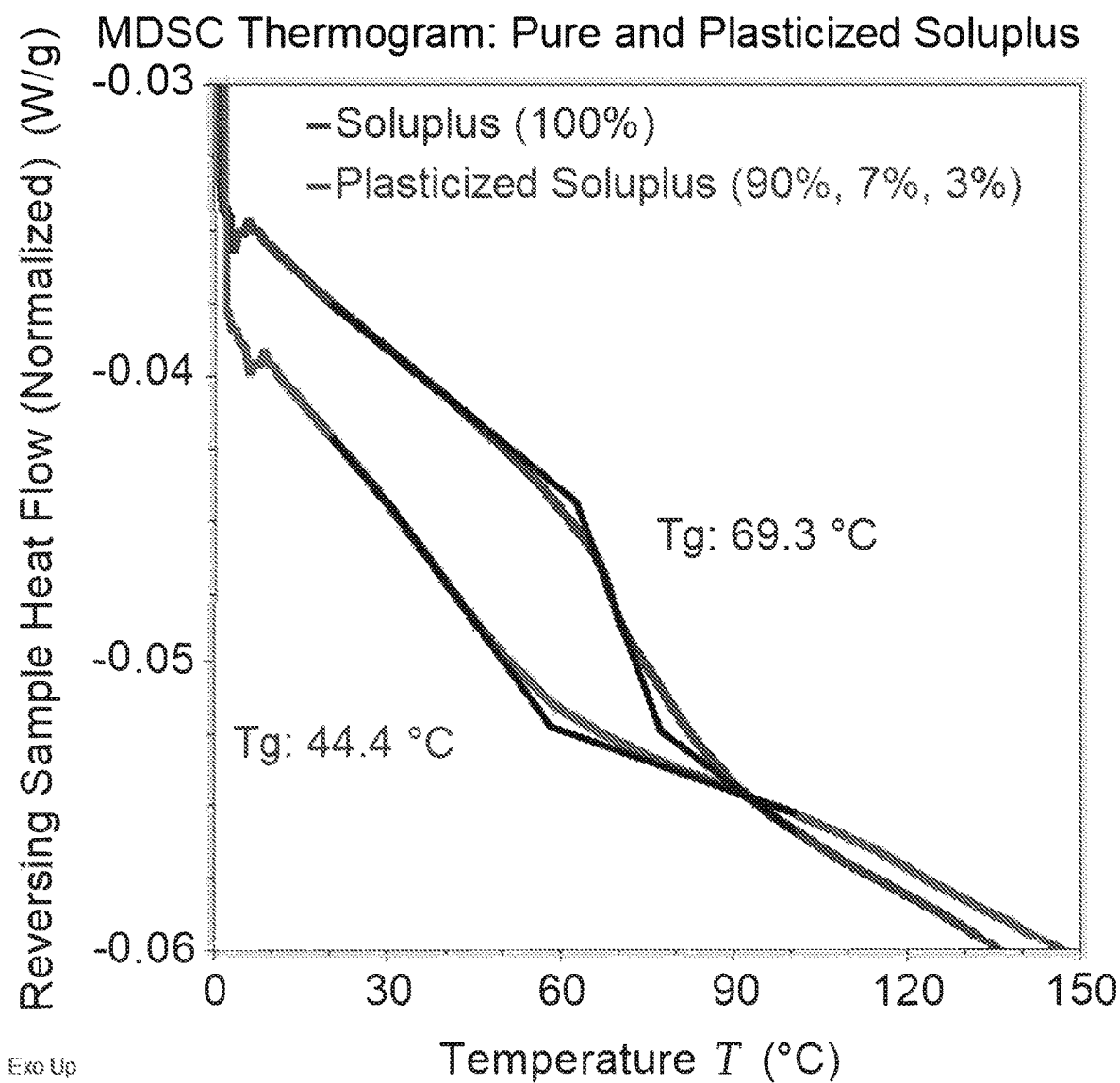
FIG. 1B shows the results of modulated DSC thermogram of pure and plasticized Soluplus®, indicating an expected lowering of the $T_g$.
Figure 1C:
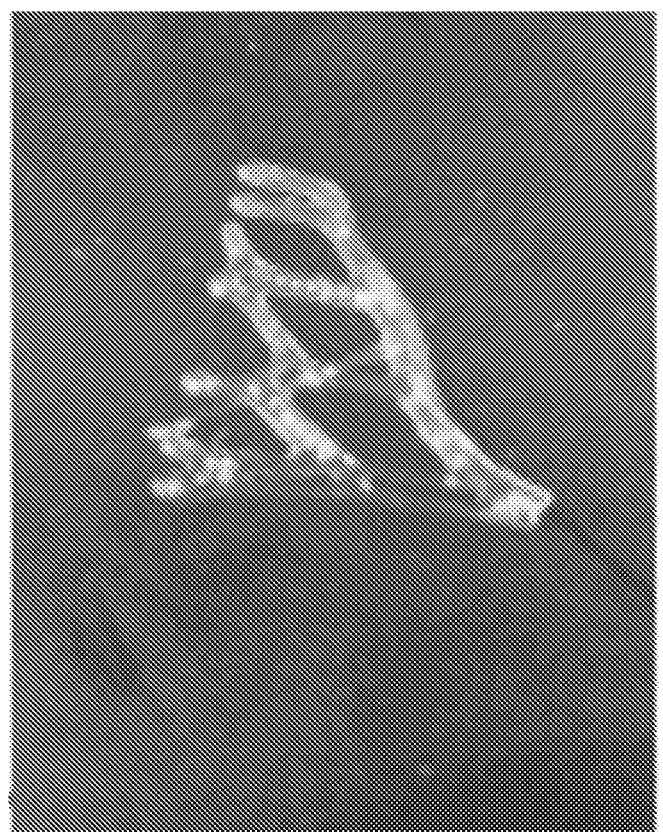
FIG. 1C shows a representative printed thermoresponsive sacrificial template with branching structure (approximately 1 cm×1 cm).

Representative examples of extruded filament (with a 1.75 mm diameter) is shown in FIG. 1A. A polymer blend of 90% Soluplus®, 7% PEG Mw 300, 3% PEG Mw 100,000 (all weight percentage) was used as the plasticized Soluplus® sample. Electron microscopy were used to examine both the filament and solid printed structures to determine whether any significant phase separation is occurring. Differential scanning calorimetry was used to characterize the $T_g$ of each formulation, indicating the ability of the plasticizer to interfere with polymer-polymer interactions (FIG. 1B). Mechanical properties of the plasticized filament were characterized using an Instron 5944 load frame. In various experiments, the formulations were printed using a FlashForge Creator Pro printer with branching structure (representative results shown in FIG. 1C, 0.40 µm extrusion nozzle).

To characterize the temperature-dependent gel-to-sol transition behavior, an AR-G2 rheometer (with Peltier stage and solvent trap) was used to measure storage and loss moduli of films of the thermoresponsive formulations. The test started at elevated temperatures (~50° C.) and hydrating the solid film by adding water, phosphate buffered saline (PBS), or cell culture media in situ, then (upon reaching stable behavior indicating swelling has stopped) slowly cooling to cause the hydrated gel to disassemble. Representative results for Soluplus® are shown in in FIG. 2. The gel state modulus, disintegration (gel-to-sol) temperature, and rate were then related to the polymer film composition (thermoresponsive polymer and plasticizer mixture) and additional soluble compounds in the local environment (i.e. presence of salts, soluble factors, etc.). At some mass fraction of plasticizer, the thermoresponsive gel-to-sol transition was no longer evident.

Example 2 Tissue Culture in Hydrogel Matrix

Figure 2:
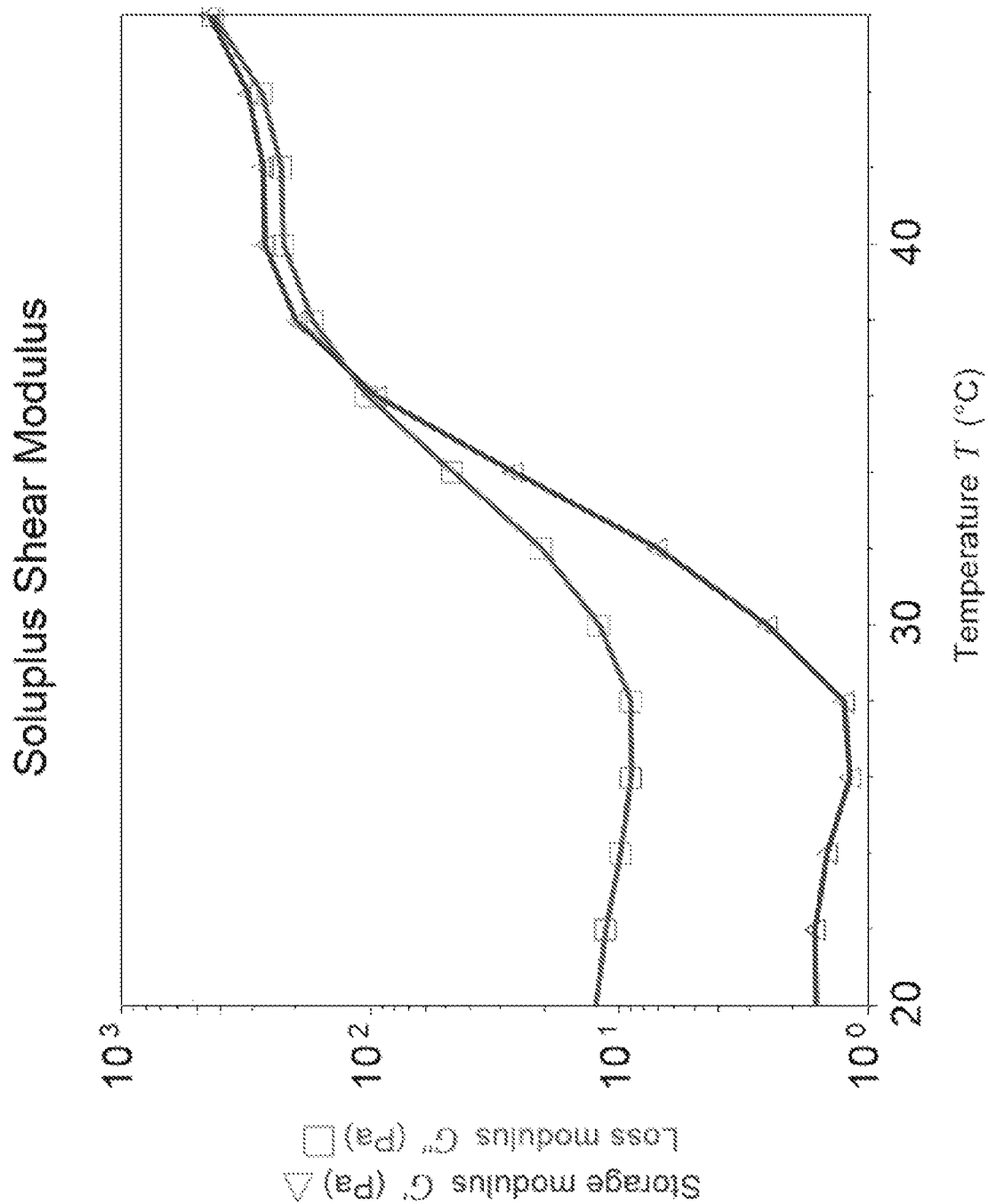
FIG. 2 shows representative results of rheological characterization of pure Soluplus® (a polyvinyl caprolactam-polyvinyl acetate-polyethylene glycol graft copolymer). Storage and loss moduli as a function of decreasing temperature was measured, highlighting the gel-to-sol transition that occurs around 37° C.
Figures 3A, 3B, 3C, 3D, 3E, 3F:
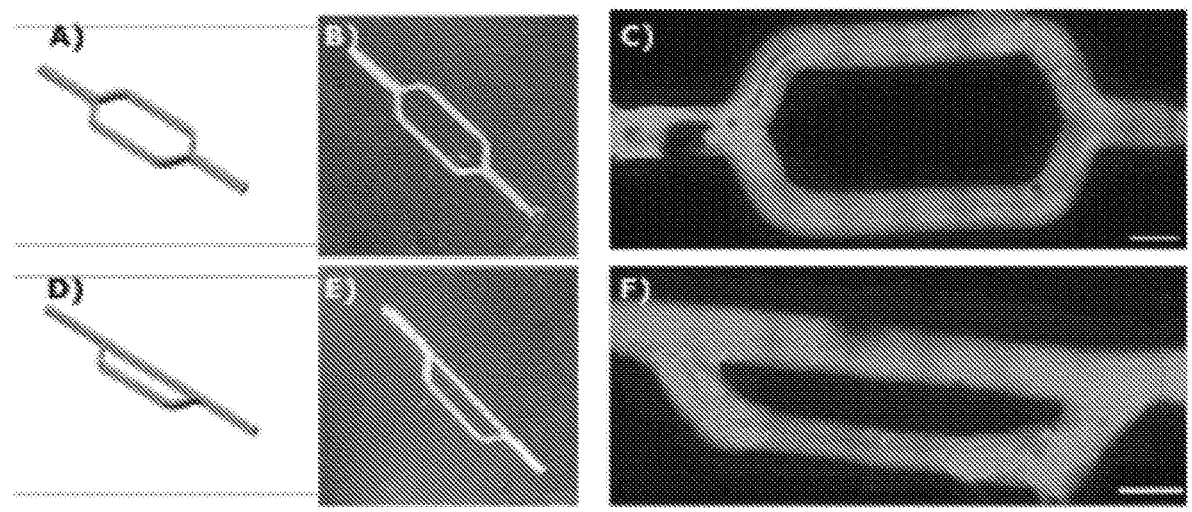
FIGS. 3A-3F show the representative branching channels formed by the printed template structures in gelatin cross-linked with microbial transglutaminase.
Figure 3G:
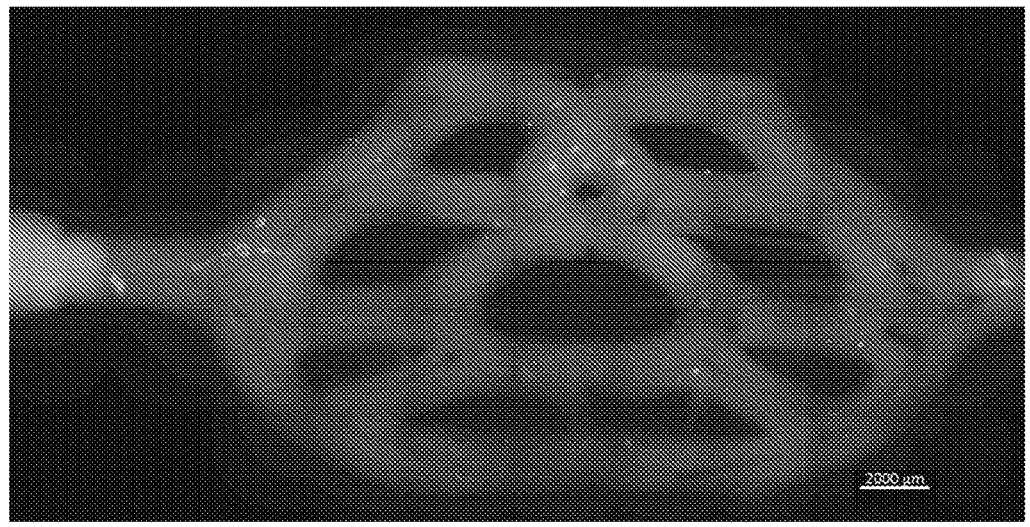
FIG. 3G shows more complex channels formed from FDM-printed thermoresponsive structures.

Plasticized Soluplus® was printed as described above. Printed structures were embedded within 10% (w/v) porcine gelatin containing 1% microbial transglutaminase. After casting the gelatin, the composite structure was placed in a 37° C. incubator to accelerate enzymatic crosslinking. After the gel had set, the composite structure was removed from the incubator and placed in a saline bath on a rocker. As the composite structure cooled to room temperature (i.e. approximately 20° C. to 25° C.), the Soluplus® template dissolved (gel-to-sol transition, as indicated in FIG. 2), leaving behind channel structures. FIGS. 3A-3G show the representative branching channels formed by the printed template structures in gelatin crosslinked with microbial transglutaminase.

Figure 4:
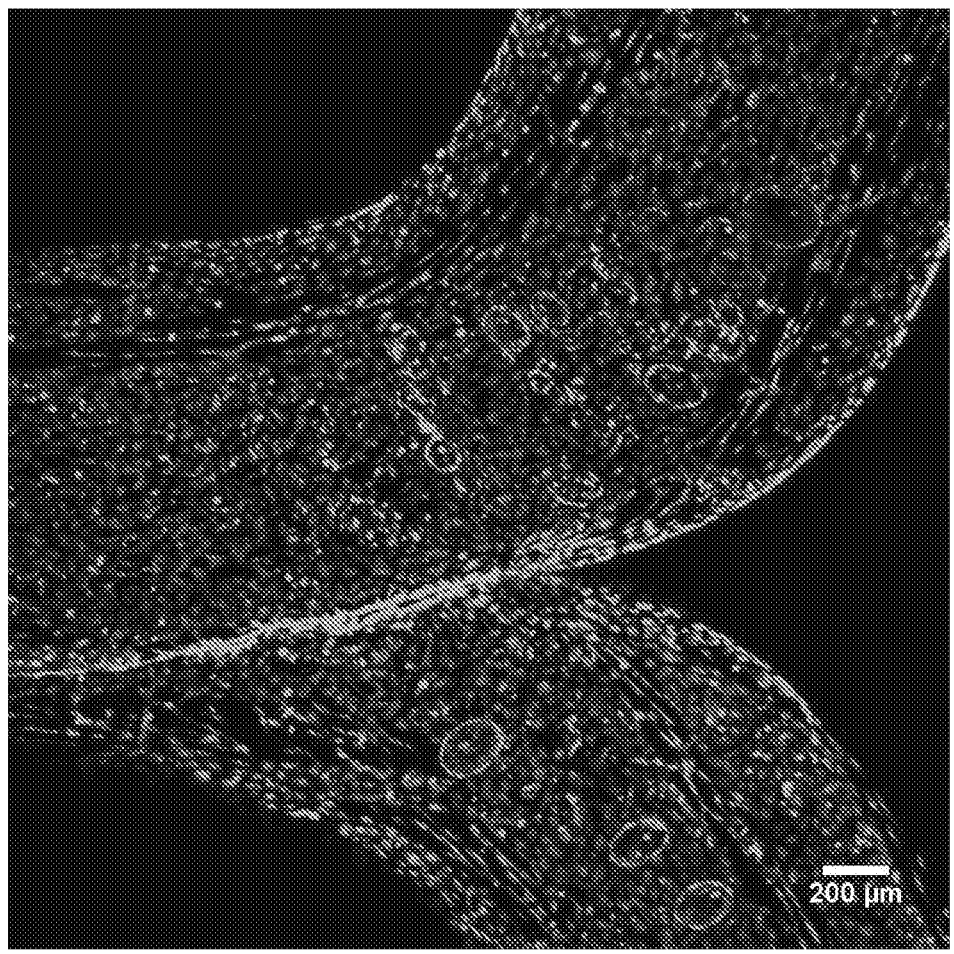
FIG. 4 shows green fluorescent protein (GFP) expressing human umbilical vein endothelial cells (HUVECs) seeded on the inner walls of branching channels (FIGS. 1A-IC) defined in enzymatically crosslinked gelatin using sacrificial FDM-printed Soluplus®.

Green fluorescent protein-expressing human umbilical vein endothelial cells (GFP-HUVECs) were introduced into the channels within the gelatin hydrogel and allowed to adhere for at least 1 hour. Subsequently, the channel was perfused with cell culture media, facilitating cell viability and proliferation. These polymer materials did not demonstrate significant cytotoxicity in these experiments, and when removed from a gelatin gel formed a surface appropriate for cell adhesion and growth (representative results shown in FIG. 4).

Figure 5:
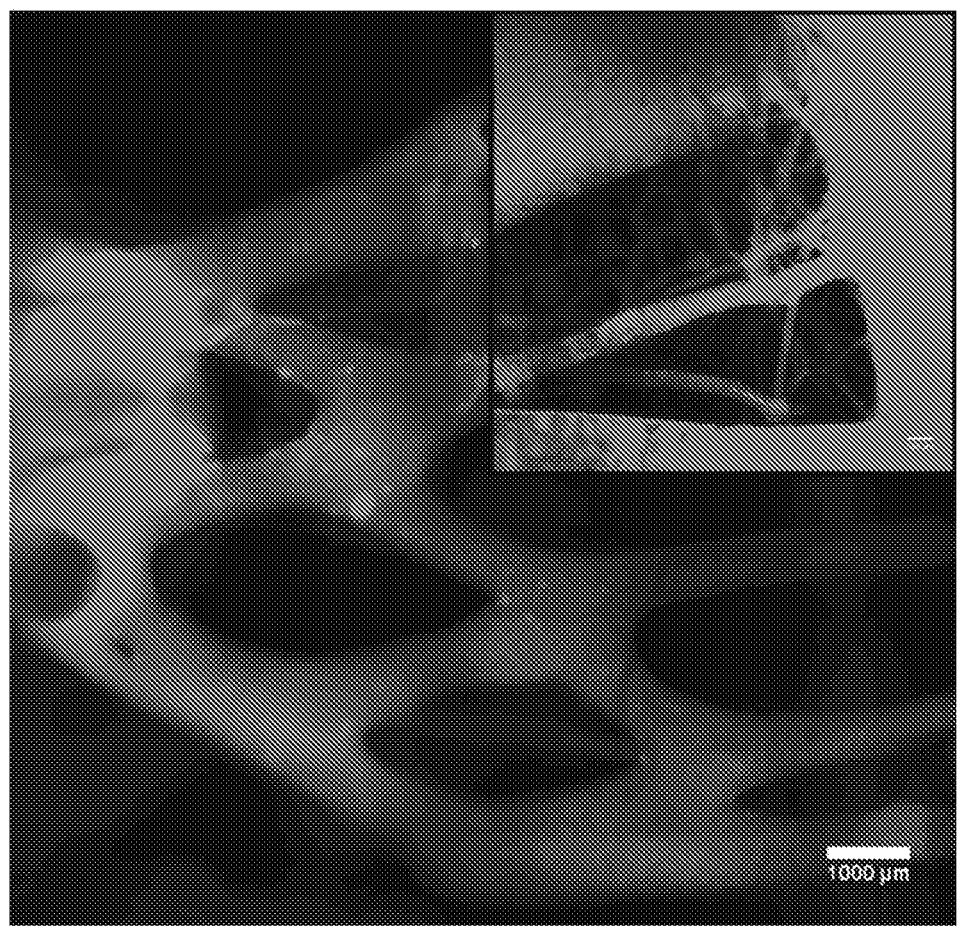
FIG. 5 shows a representative fluorescence microscopy image of red fluorescent beads flowing in a channel network formed by a hybrid approach employing FDM-printed thermoresponsive sacrificial templates and solvent-spun thermoresponsive sacrificial microfibers. The inset in the upper right shows a higher magnification view indicating the interface between the printed channels and the fiber-formed channels (insert scale bar is 100 µm).

In another experiment, the printed sacrificial template was welded to a microfibrous mesh of Soluplus®, and the gelatin solution cast over this hybrid sacrificial template. The resulting channel system consisted of both larger channels defined by the FDM-printed template, and smaller channels defined by the microfibrous mesh (representative results shown in FIG. 5). This approach produced a network of channels with diameters ranging from below 50 µm to millimeter scale.

It is understood that the foregoing detailed description and accompanying examples are merely illustrative and are not to be taken as limitations upon the scope of the invention, which is defined solely by the following claims.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for preparing a solid scaffold, the method comprising: printing a biocompatible polymer composition comprising a thermoresponsive polymer using a fused deposition modelling printer to form the solid scaffold, wherein the biocompatible polymer composition has a disintegration temperature of about 4° C. to about 37° C., wherein the polymer composition is in a solid or gel state above the disintegration temperature, and wherein the polymer composition is in a liquid state below the disintegration temperature.

2. The method claim 1, wherein the thermoresponsive polymer comprises a monomer selected from the group consisting of N-isopropylacrylamide, N,N-diethylacrylamide, 2-(dimethylamino)ethyl methacrylate, glucose, O-methyl glucose, lactic acid, glycolic acid, caprolactone, vinyl caprolactam, vinyl acetate, ethylene glycol, and a combination thereof.

3. The method of claim 1, wherein the thermoresponsive polymer comprises poly(N-isopropylacrylamide), poly(N,N-diethylacrylamide), poly[2-(dimethylamino)ethyl methacrylate], methylcellulose, poly(N-vinylcaprolacatam), a copolymer of N-isopropylacrylamide with one or more monomer selected from the group consisting of acrylamide, N-tert-butylacrylamide, acrylic acid, and allylamine, a copolymer comprising at least one monomer selected from group consisting of vinyl caprolactam, caprolactone, vinyl acetate, and ethylene glycol, or a combination thereof.

4. The method of claim 1, wherein the polymer composition further comprises a plasticizer.

5. The method of claim 1, wherein the printing is performed at a temperature of about 50° C. to about 250° C.

6. The method of claim 1, wherein the solid scaffold comprises vascular branches having a diameter of about 50 µm to about 5 mm, wherein the vascular branches define a three-dimensional vascular structure.

7. The method of claim 1, wherein the thermoresponsive polymer comprises a polyvinyl caprolactam-polyvinyl acetate-polyethylene glycol graft copolymer.

8. The method of claim 4, wherein the ratio of the thermoresponsive polymer to the plasticizer is about 50:50 to about 99:1 by weight.

* * * * *